(12) United States Patent
Ducharme

(10) Patent No.: US 8,647,368 B2
(45) Date of Patent: Feb. 11, 2014

(54) TISSUE ANCHORS AND MEDICAL DEVICES FOR RAPID DEPLOYMENT OF TISSUE ANCHORS

(75) Inventor: Richard W. Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 323 days.

(21) Appl. No.: 12/753,110

(22) Filed: Apr. 2, 2010

(65) Prior Publication Data

US 2010/0256678 A1  Oct. 7, 2010

Related U.S. Application Data

(60) Provisional application No. 61/166,364, filed on Apr. 3, 2009.

(51) Int. Cl.
*A61B 17/04* (2006.01)
(52) U.S. Cl.
USPC .......................................................... 606/232
(58) Field of Classification Search
USPC ............. 606/232, 138, 139, 144, 2, 153, 167; 600/104
See application file for complete search history.

(56) References Cited

U.S. PATENT DOCUMENTS

| | | | |
|---|---|---|---|
| 775,985 A | 11/1904 | McKain | |
| 1,037,864 A | 9/1912 | Carlson | |
| 1,521,396 A | 12/1924 | Scott | |
| 2,199,025 A | 4/1940 | Conn | |
| 2,609,155 A | 9/1952 | Fosnaugh | |
| 2,880,728 A | 4/1959 | Rights | |
| 3,470,875 A | 10/1969 | Johnson | |
| 3,513,848 A | 5/1970 | Winston et al. | |
| 3,556,079 A | 1/1971 | Omizo | |
| 3,664,345 A | 5/1972 | Dabbs et al. | |
| 3,710,400 A | 1/1973 | Sparks | |
| 3,766,610 A | 10/1973 | Thorsbakken | |

(Continued)

FOREIGN PATENT DOCUMENTS

| | | |
|---|---|---|
| EP | 0643945 | 3/1995 |
| EP | 0774237 A2 | 5/1997 |

(Continued)

OTHER PUBLICATIONS

International Search Report/Written Opinion for PCT/US2010/029798.

(Continued)

*Primary Examiner* — S. Thomas Hughes
*Assistant Examiner* — Tin Nguyen
(74) *Attorney, Agent, or Firm* — Brinks Gilson & Lione

(57) ABSTRACT

Medical devices and related methods are provided for closing a perforation in a bodily wall. The medical device generally includes a set of tissue anchors and an elongate tensioning member. Each anchor includes a crossbar having opposing ends and defining a longitudinal axis. A strand is connected to the crossbar at a location between the opposing ends and projects away from the longitudinal axis. The strand includes a distal end connected to the crossbar and a proximal end having a first connector. The elongate tensioning member is structured to selectively engage and disengage the first connector. The strands of the anchor are capable of being tensioned and fixed together for closing the perforation. The tensioning member is removed after the strands are fixed together.

15 Claims, 6 Drawing Sheets

(56) References Cited

U.S. PATENT DOCUMENTS

| | | | |
|---|---|---|---|
| 3,856,016 A | 12/1974 | Davis |
| 3,870,048 A | 3/1975 | Yoon |
| 3,911,923 A | 10/1975 | Yoon |
| 3,952,377 A | 4/1976 | Morell |
| 3,954,108 A | 5/1976 | Davis |
| 3,967,625 A | 7/1976 | Yoon |
| 3,989,049 A | 11/1976 | Yoon |
| 4,059,333 A | 11/1977 | Mixon, Jr. |
| 4,085,743 A | 4/1978 | Yoon |
| 4,103,680 A | 8/1978 | Yoon |
| 4,235,238 A | 11/1980 | Ogiu et al. |
| 4,236,470 A | 12/1980 | Stenson |
| 4,374,523 A | 2/1983 | Yoon |
| 4,448,194 A | 5/1984 | DiGiovanni et al. |
| 4,532,926 A | 8/1985 | O'Holla |
| 4,539,716 A | 9/1985 | Bell |
| 4,604,094 A | 8/1986 | Shook |
| 4,635,638 A | 1/1987 | Weintraub et al. |
| 4,669,473 A | 6/1987 | Richards et al. |
| 4,719,671 A | 1/1988 | Ito et al. |
| 4,738,740 A | 4/1988 | Pinchuk |
| 4,749,114 A | 6/1988 | Green |
| 4,773,420 A | 9/1988 | Green |
| 4,798,606 A | 1/1989 | Pinchuk |
| 4,821,939 A | 4/1989 | Green |
| 4,890,615 A | 1/1990 | Caspari et al. |
| 4,927,410 A | 5/1990 | Kovacs |
| 5,015,250 A | 5/1991 | Foster |
| 5,053,043 A | 10/1991 | Gottesman et al. |
| 5,059,201 A | 10/1991 | Asnis |
| 5,084,057 A | 1/1992 | Green et al. |
| 5,123,914 A | 6/1992 | Cope |
| 5,203,787 A | 4/1993 | Noblitt et al. |
| 5,222,508 A | 6/1993 | Contarini |
| 5,254,126 A | 10/1993 | Filipi et al. |
| 5,258,000 A | 11/1993 | Gianturco |
| 5,258,015 A | 11/1993 | Li et al. |
| 5,281,237 A | 1/1994 | Gimpelson |
| 5,282,832 A | 2/1994 | Toso et al. |
| 5,304,184 A | 4/1994 | Hathaway et al. |
| 5,310,407 A | 5/1994 | Casale |
| 5,316,543 A | 5/1994 | Eberbach |
| 5,318,221 A | 6/1994 | Green et al. |
| 5,320,630 A | 6/1994 | Ahmed |
| 5,320,632 A | 6/1994 | Heidmueller |
| 5,333,624 A | 8/1994 | Tovey |
| 5,336,229 A | 8/1994 | Noda |
| 5,350,385 A | 9/1994 | Christy |
| 5,364,408 A | 11/1994 | Gordon |
| 5,366,460 A | 11/1994 | Eberbach |
| 5,366,480 A | 11/1994 | Corriveau et al. |
| 5,368,599 A | 11/1994 | Hirsch et al. |
| 5,368,601 A | 11/1994 | Sauer et al. |
| 5,374,275 A | 12/1994 | Bradley et al. |
| 5,376,096 A | 12/1994 | Foster |
| 5,383,882 A | 1/1995 | Buess et al. |
| 5,389,103 A | 2/1995 | Meizer et al. |
| 5,391,182 A | 2/1995 | Chin |
| 5,395,381 A | 3/1995 | Green et al. |
| 5,397,331 A | 3/1995 | Himpens et al. |
| 5,403,329 A | 4/1995 | Hinchcliffe |
| 5,403,342 A | 4/1995 | Tovey et al. |
| 5,405,072 A | 4/1995 | Zlock et al. |
| 5,405,354 A | 4/1995 | Sarrett |
| 5,417,691 A | 5/1995 | Hayhurst |
| 5,417,699 A | 5/1995 | Klein et al. |
| 5,423,860 A | 6/1995 | Lizardi et al. |
| 5,439,469 A | 8/1995 | Heaven et al. |
| 5,462,558 A | 10/1995 | Kolesa et al. |
| 5,462,561 A | 10/1995 | Voda |
| 5,464,427 A | 11/1995 | Curtis et al. |
| 5,470,338 A | 11/1995 | Whitfield et al. |
| 5,476,469 A | 12/1995 | Hathaway et al. |
| 5,478,353 A | 12/1995 | Yoon |
| 5,484,451 A | 1/1996 | Akopov et al. |
| 5,486,197 A | 1/1996 | Le et al. |
| 5,503,623 A | 4/1996 | Tilton, Jr. |
| 5,507,754 A | 4/1996 | Green et al. |
| 5,520,700 A | 5/1996 | Beyar et al. |
| 5,527,343 A | 6/1996 | Bonutti |
| 5,531,763 A | 7/1996 | Mastri et al. |
| 5,549,617 A | 8/1996 | Green et al. |
| 5,554,183 A | 9/1996 | Nazari |
| 5,556,402 A | 9/1996 | Xu |
| 5,562,683 A | 10/1996 | Chan |
| 5,562,688 A | 10/1996 | Riza |
| 5,571,090 A | 11/1996 | Sherts |
| 5,571,119 A | 11/1996 | Atala |
| 5,573,540 A | 11/1996 | Yoon |
| 5,573,543 A | 11/1996 | Akopov et al. |
| 5,578,044 A | 11/1996 | Gordon et al. |
| 5,584,835 A | 12/1996 | Greenfield |
| 5,586,986 A | 12/1996 | Hinchliffe |
| 5,601,557 A * | 2/1997 | Hayhurst .................. 606/232 |
| 5,609,597 A | 3/1997 | Lehrer |
| 5,626,590 A | 5/1997 | Wilk |
| 5,630,824 A | 5/1997 | Hart |
| 5,643,292 A | 7/1997 | Hart |
| 5,643,317 A | 7/1997 | Pavcnik et al. |
| 5,645,552 A | 7/1997 | Sherts |
| 5,653,717 A | 8/1997 | Ko et al. |
| 5,662,683 A | 9/1997 | Kay |
| 5,683,402 A | 11/1997 | Cosgrove et al. |
| 5,690,656 A | 11/1997 | Cope et al. |
| 5,693,060 A | 12/1997 | Martin |
| 5,700,273 A | 12/1997 | Buelna et al. |
| 5,707,379 A | 1/1998 | Fleenor et al. |
| 5,709,694 A | 1/1998 | Greenberg et al. |
| 5,728,113 A | 3/1998 | Sherts |
| 5,741,277 A | 4/1998 | Gordon et al. |
| 5,741,278 A | 4/1998 | Stevens |
| 5,746,751 A | 5/1998 | Sherts |
| 5,769,862 A | 6/1998 | Kammerer et al. |
| 5,788,625 A | 8/1998 | Plouhar et al. |
| 5,792,153 A | 8/1998 | Swain et al. |
| 5,810,848 A | 9/1998 | Hayhurst |
| 5,824,010 A | 10/1998 | McDonald |
| 5,836,955 A | 11/1998 | Buelna et al. |
| 5,836,956 A | 11/1998 | Buelna et al. |
| 5,846,253 A | 12/1998 | Buelna et al. |
| 5,860,990 A | 1/1999 | Nobis et al. |
| 5,865,791 A | 2/1999 | Whayne et al. |
| 5,865,836 A | 2/1999 | Miller |
| 5,891,159 A | 4/1999 | Sherman et al. |
| 5,902,228 A | 5/1999 | Schulsinger et al. |
| 5,908,428 A | 6/1999 | Scirica et al. |
| 5,919,184 A | 7/1999 | Tilton, Jr. |
| 5,931,844 A | 8/1999 | Thompson et al. |
| 5,938,668 A | 8/1999 | Scirica et al. |
| 5,947,997 A | 9/1999 | Pavcnik et al. |
| 5,948,000 A | 9/1999 | Larsen et al. |
| 5,957,937 A | 9/1999 | Yoon |
| 5,968,078 A | 10/1999 | Grotz |
| 6,010,525 A | 1/2000 | Bonutti et al. |
| 6,036,699 A | 3/2000 | Andreas et al. |
| 6,068,648 A | 5/2000 | Cole et al. |
| 6,077,217 A | 6/2000 | Love et al. |
| 6,086,601 A | 7/2000 | Yoon |
| 6,086,608 A | 7/2000 | Ek et al. |
| 6,099,553 A | 8/2000 | Hart et al. |
| 6,110,183 A | 8/2000 | Cope |
| RE36,974 E | 11/2000 | Bonutti |
| 6,200,329 B1 | 3/2001 | Fung et al. |
| 6,290,674 B1 | 9/2001 | Roue et al. |
| 6,293,961 B2 | 9/2001 | Schwartz et al. |
| 6,319,271 B1 | 11/2001 | Schwartz et al. |
| 6,328,727 B1 | 12/2001 | Frazier et al. |
| 6,348,059 B1 | 2/2002 | Hathaway et al. |
| 6,355,050 B1 | 3/2002 | Andreas et al. |
| 6,419,669 B1 | 7/2002 | Frazier et al. |
| 6,423,087 B1 | 7/2002 | Sawada |
| 6,432,123 B2 | 8/2002 | Schwartz et al. |
| 6,482,178 B1 | 11/2002 | Andrews et al. |
| 6,491,707 B2 | 12/2002 | Makower et al. |

(56) References Cited

U.S. PATENT DOCUMENTS

| | | | |
|---|---|---|---|
| 6,551,333 B2 | 4/2003 | Kuhns et al. |
| 6,572,629 B2 | 6/2003 | Kalloo et al. |
| 6,592,559 B1 | 7/2003 | Pakter et al. |
| 6,610,026 B2 | 8/2003 | Cragg et al. |
| 6,635,073 B2* | 10/2003 | Bonutti .......... 606/232 |
| 6,641,557 B1 | 11/2003 | Frazier et al. |
| 6,699,263 B2 | 3/2004 | Cope |
| 6,712,804 B2 | 3/2004 | Roue et al. |
| 6,719,763 B2 | 4/2004 | Chung et al. |
| 6,746,472 B2 | 6/2004 | Frazier et al. |
| 6,755,843 B2 | 6/2004 | Chung et al. |
| 6,840,953 B2 | 1/2005 | Martinek |
| 6,955,643 B2 | 10/2005 | Gellman et al. |
| 6,966,916 B2 | 11/2005 | Kumar |
| 6,972,027 B2 | 12/2005 | Fallin et al. |
| 6,974,466 B2 | 12/2005 | Ahmed et al. |
| 6,988,987 B2 | 1/2006 | Ishikawa |
| 6,997,931 B2 | 2/2006 | Sauer et al. |
| 7,025,756 B2 | 4/2006 | Frazier et al. |
| 7,033,379 B2 | 4/2006 | Peterson |
| 7,033,380 B2 | 4/2006 | Schwartz et al. |
| 7,056,325 B1 | 6/2006 | Makower et al. |
| 7,060,078 B2 | 6/2006 | Hathaway et al. |
| 7,060,084 B1 | 6/2006 | Loshakove et al. |
| 7,081,124 B2 | 7/2006 | Sancoff et al. |
| 7,087,073 B2 | 8/2006 | Bonutti |
| 7,101,862 B2 | 9/2006 | Cochrum et al. |
| 7,112,207 B2 | 9/2006 | Allen et al. |
| 7,115,110 B2 | 10/2006 | Frazier et al. |
| 7,118,583 B2 | 10/2006 | O'Quinn et al. |
| 7,122,039 B2 | 10/2006 | Chu |
| 7,122,040 B2 | 10/2006 | Hill et al. |
| 7,144,401 B2 | 12/2006 | Yamamoto et al. |
| 7,147,652 B2 | 12/2006 | Bonutti et al. |
| 7,156,880 B2 | 1/2007 | Evans et al. |
| 7,157,636 B2 | 1/2007 | Hsieh |
| 7,166,116 B2 | 1/2007 | Lizardi et al. |
| 7,175,636 B2 | 2/2007 | Yamamoto et al. |
| 7,217,279 B2 | 5/2007 | Reese |
| 7,232,448 B2 | 6/2007 | Battles et al. |
| RE39,841 E | 9/2007 | Bilotti |
| 7,273,451 B2 | 9/2007 | Sekine et al. |
| 7,300,451 B2 | 11/2007 | Crombie et al. |
| 7,316,706 B2 | 1/2008 | Bloom et al. |
| 7,323,004 B2 | 1/2008 | Parahar |
| 7,326,221 B2 | 2/2008 | Sakamoto |
| 7,326,231 B2 | 2/2008 | Phillips et al. |
| 7,331,968 B2 | 2/2008 | Arp et al. |
| 7,335,221 B2 | 2/2008 | Collier et al. |
| 7,344,545 B2 | 3/2008 | Takemoto et al. |
| RE40,237 E | 4/2008 | Bilotti et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,371,244 B2 | 5/2008 | Chatlynne et al. |
| 7,380,695 B2 | 6/2008 | Doll et al. |
| 7,380,696 B2 | 6/2008 | Shelton, IV et al. |
| 7,390,329 B2 | 6/2008 | Westra et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,077 B2 | 8/2008 | Ortiz et al. |
| 7,407,505 B2 | 8/2008 | Sauer et al. |
| 7,410,086 B2 | 8/2008 | Ortiz et al. |
| 7,416,101 B2 | 8/2008 | Shelton, IV et al. |
| 7,416,554 B2 | 8/2008 | Lam et al. |
| D576,278 S | 9/2008 | Nalagatla et al. |
| 7,419,080 B2 | 9/2008 | Smith et al. |
| 7,422,139 B2 | 9/2008 | Shelton, IV et al. |
| 7,494,496 B2 | 2/2009 | Swain et al. |
| 7,601,159 B2 | 10/2009 | Ewers et al. |
| 7,618,426 B2 | 11/2009 | Ewers et al. |
| 7,621,925 B2 | 11/2009 | Saadat et al. |
| 7,622,068 B2 | 11/2009 | Li et al. |
| 7,641,836 B2 | 1/2010 | Li et al. |
| 7,674,275 B2 | 3/2010 | Martin et al. |
| 7,678,135 B2 | 3/2010 | Maahs et al. |
| 7,695,493 B2 | 4/2010 | Saadat et al. |
| 7,704,264 B2 | 4/2010 | Ewers et al. |
| 7,736,376 B2 | 6/2010 | Sato et al. |
| 7,736,378 B2 | 6/2010 | Maahs et al. |
| 7,736,379 B2 | 6/2010 | Ewers et al. |
| 7,744,613 B2 | 6/2010 | Ewers et al. |
| 7,758,598 B2 | 7/2010 | Conlon et al. |
| 7,780,702 B2 | 8/2010 | Shiono |
| 7,785,348 B2 | 8/2010 | Kuhns et al. |
| 7,815,659 B2 | 10/2010 | Conlon et al. |
| 7,815,662 B2 | 10/2010 | Spivey et al. |
| 2002/0087188 A1* | 7/2002 | Pedlick et al. .......... 606/232 |
| 2002/0116010 A1 | 8/2002 | Chung et al. |
| 2002/0116011 A1 | 8/2002 | Chee Chung et al. |
| 2002/0198542 A1 | 12/2002 | Yamamoto et al. |
| 2003/0045891 A1 | 3/2003 | Yamamoto et al. |
| 2003/0181924 A1 | 9/2003 | Yamamoto et al. |
| 2003/0216613 A1 | 11/2003 | Suzuki et al. |
| 2004/0147941 A1* | 7/2004 | Takemoto et al. .......... 606/144 |
| 2004/0147958 A1 | 7/2004 | Lam et al. |
| 2004/0153074 A1 | 8/2004 | Bojarski et al. |
| 2004/0167546 A1 | 8/2004 | Saadat et al. |
| 2004/0186514 A1 | 9/2004 | Swain et al. |
| 2004/0220596 A1 | 11/2004 | Frazier et al. |
| 2004/0243179 A1 | 12/2004 | Foerster |
| 2005/0004584 A1 | 1/2005 | Franco et al. |
| 2005/0113851 A1 | 5/2005 | Swain et al. |
| 2005/0143762 A1 | 6/2005 | Paraschac et al. |
| 2005/0149067 A1 | 7/2005 | Takemoto et al. |
| 2005/0171562 A1 | 8/2005 | Criscuolo et al. |
| 2005/0197594 A1 | 9/2005 | Burbank et al. |
| 2005/0251165 A1 | 11/2005 | Vaughan et al. |
| 2005/0251166 A1 | 11/2005 | Vaughan et al. |
| 2005/0277945 A1 | 12/2005 | Saadat et al. |
| 2005/0277957 A1 | 12/2005 | Kuhns et al. |
| 2005/0277981 A1 | 12/2005 | Maahs et al. |
| 2006/0002852 A1 | 1/2006 | Saltzman et al. |
| 2006/0004409 A1 | 1/2006 | Nobis et al. |
| 2006/0004410 A1 | 1/2006 | Nobis et al. |
| 2006/0015006 A1 | 1/2006 | Laurence et al. |
| 2006/0015125 A1 | 1/2006 | Swain |
| 2006/0020274 A1 | 1/2006 | Ewers et al. |
| 2006/0020277 A1 | 1/2006 | Gostout et al. |
| 2006/0025819 A1 | 2/2006 | Nobis et al. |
| 2006/0036267 A1 | 2/2006 | Saadat et al. |
| 2006/0135989 A1 | 6/2006 | Carley et al. |
| 2006/0155288 A1 | 7/2006 | Little et al. |
| 2006/0167482 A1 | 7/2006 | Swain et al. |
| 2006/0190016 A1 | 8/2006 | Onuki et al. |
| 2006/0206063 A1 | 9/2006 | Kagan et al. |
| 2006/0217762 A1 | 9/2006 | Maahs et al. |
| 2006/0235447 A1 | 10/2006 | Walshe |
| 2006/0237022 A1 | 10/2006 | Chen et al. |
| 2006/0237023 A1 | 10/2006 | Cox et al. |
| 2006/0241691 A1 | 10/2006 | Wilk |
| 2006/0253144 A1 | 11/2006 | Mikkaichi |
| 2006/0265010 A1 | 11/2006 | Paraschac et al. |
| 2006/0271073 A1 | 11/2006 | Lam et al. |
| 2006/0271101 A1 | 11/2006 | Saadat et al. |
| 2006/0282089 A1 | 12/2006 | Stokes et al. |
| 2006/0286664 A1 | 12/2006 | McAllister et al. |
| 2007/0010835 A1 | 1/2007 | Breton et al. |
| 2007/0027476 A1 | 2/2007 | Harries et al. |
| 2007/0049970 A1* | 3/2007 | Belef et al. .......... 606/232 |
| 2007/0093858 A1 | 4/2007 | Gambale et al. |
| 2007/0100375 A1 | 5/2007 | Mikkaichi et al. |
| 2007/0100376 A1 | 5/2007 | Mikkaichi et al. |
| 2007/0106313 A1 | 5/2007 | Golden et al. |
| 2007/0112362 A1 | 5/2007 | Mikkaichi et al. |
| 2007/0123840 A1 | 5/2007 | Cox |
| 2007/0162052 A1 | 7/2007 | Hashimoto et al. |
| 2007/0191886 A1 | 8/2007 | Dejima et al. |
| 2007/0197864 A1 | 8/2007 | Dejima et al. |
| 2007/0198000 A1 | 8/2007 | Miyamoto et al. |
| 2007/0208360 A1 | 9/2007 | Demarais et al. |
| 2007/0213702 A1 | 9/2007 | Kogasaka et al. |
| 2007/0219411 A1 | 9/2007 | Dejima et al. |

(56) References Cited

U.S. PATENT DOCUMENTS

| | | |
|---|---|---|
| 2007/0255296 A1 | 11/2007 | Sauer |
| 2007/0270752 A1 | 11/2007 | LaBombard |
| 2007/0270889 A1 | 11/2007 | Conlon et al. |
| 2007/0276416 A1 | 11/2007 | Ginn et al. |
| 2007/0276424 A1 | 11/2007 | Mikkaichi et al. |
| 2008/0009888 A1 | 1/2008 | Ewers et al. |
| 2008/0027272 A1 | 1/2008 | Kadykowski |
| 2008/0048002 A1 | 2/2008 | Smith et al. |
| 2008/0058710 A1 | 3/2008 | Wilk |
| 2008/0058865 A1 | 3/2008 | Wilk |
| 2008/0065157 A1 | 3/2008 | Crombie et al. |
| 2008/0086153 A1 | 4/2008 | Sakamoto et al. |
| 2008/0097489 A1 | 4/2008 | Goldfarb et al. |
| 2008/0114378 A1 | 5/2008 | Matsushita |
| 2008/0114379 A1 | 5/2008 | Takemoto et al. |
| 2008/0114380 A1 | 5/2008 | Takemoto et al. |
| 2008/0114398 A1 | 5/2008 | Phillips et al. |
| 2008/0140095 A1 | 6/2008 | Smith et al. |
| 2008/0147116 A1 | 6/2008 | Smith et al. |
| 2008/0154290 A1 | 6/2008 | Golden et al. |
| 2008/0172088 A1 | 7/2008 | Smith et al. |
| 2008/0177304 A1 | 7/2008 | Westra et al. |
| 2008/0185752 A1 | 8/2008 | Cerwin et al. |
| 2008/0200930 A1 | 8/2008 | Saadat et al. |
| 2008/0208161 A1 | 8/2008 | Kaji et al. |
| 2008/0208214 A1 | 8/2008 | Sato et al. |
| 2008/0208218 A1 | 8/2008 | Shiono |
| 2008/0208219 A1 | 8/2008 | Suzuki |
| 2008/0208220 A1 | 8/2008 | Shiono et al. |
| 2008/0208251 A1 | 8/2008 | Weadock et al. |
| 2008/0221619 A1 | 9/2008 | Spivey et al. |
| 2008/0228199 A1 | 9/2008 | Cropper et al. |
| 2008/0228202 A1 | 9/2008 | Cropper et al. |
| 2008/0228203 A1 | 9/2008 | Bell et al. |
| 2008/0243148 A1 | 10/2008 | Mikkaichi et al. |
| 2008/0255422 A1 | 10/2008 | Kondoh et al. |
| 2008/0255423 A1 | 10/2008 | Kondo et al. |
| 2008/0255427 A1 | 10/2008 | Satake et al. |
| 2008/0262525 A1 | 10/2008 | Chang et al. |
| 2008/0269566 A1 | 10/2008 | Measamer |
| 2008/0275297 A1 | 11/2008 | Bakos et al. |
| 2008/0296344 A1 | 12/2008 | Cropper et al. |
| 2008/0300547 A1 | 12/2008 | Bakos |
| 2008/0300627 A1 | 12/2008 | Measamer et al. |
| 2008/0300629 A1 | 12/2008 | Surti |
| 2008/0319257 A1 | 12/2008 | Sato et al. |
| 2009/0005800 A1 | 1/2009 | Franer et al. |
| 2009/0018552 A1 | 1/2009 | Lam et al. |
| 2009/0024163 A1 | 1/2009 | Zeiner et al. |
| 2009/0069847 A1 | 3/2009 | Hashiba et al. |
| 2009/0076527 A1 | 3/2009 | Miyamoto et al. |
| 2009/0088780 A1 | 4/2009 | Shiono et al. |
| 2009/0088797 A1 | 4/2009 | Crombie et al. |
| 2009/0125038 A1 | 5/2009 | Ewers et al. |
| 2009/0125039 A1 | 5/2009 | Mikkaichi et al. |
| 2009/0204147 A1 | 8/2009 | Rahmani |
| 2009/0299406 A1 | 12/2009 | Swain et al. |
| 2009/0326561 A1 | 12/2009 | Carroll, II et al. |
| 2009/0326578 A1 | 12/2009 | Ewers et al. |
| 2010/0010457 A1 | 1/2010 | Ewers et al. |
| 2010/0042115 A1 | 2/2010 | Saadar et al. |
| 2010/0042144 A1 | 2/2010 | Bennett |
| 2010/0049213 A1 | 2/2010 | Serina et al. |
| 2010/0076462 A1 | 3/2010 | Bakos et al. |
| 2010/0076488 A1 | 3/2010 | Spivey et al. |
| 2010/0094083 A1 | 4/2010 | Taylor et al. |
| 2010/0094341 A1 | 4/2010 | Raju |
| 2010/0106166 A1 | 4/2010 | Cropper et al. |
| 2010/0113873 A1 | 5/2010 | Suzuki et al. |
| 2010/0121349 A1 | 5/2010 | Meier et al. |
| 2010/0174296 A1 | 7/2010 | Vakharia et al. |
| 2010/0174312 A1 | 7/2010 | Maahs et al. |
| 2010/0198192 A1 | 8/2010 | Serina et al. |
| 2010/0211086 A1 | 8/2010 | Ewers et al. |
| 2010/0256679 A1 | 10/2010 | Ducharme |
| 2010/0268253 A1 | 10/2010 | Ahlberg et al. |

FOREIGN PATENT DOCUMENTS

| | | |
|---|---|---|
| EP | 1484021 A1 | 12/2004 |
| EP | 1598018 A1 | 11/2005 |
| EP | 1602336 A1 | 12/2005 |
| EP | 1938760 A1 | 7/2008 |
| EP | 2042105 A2 | 4/2009 |
| WO | WO 9904699 | 2/1999 |
| WO | WO 0110312 A1 | 2/2001 |
| WO | WO 0139671 | 6/2001 |
| WO | WO 0154585 | 8/2001 |
| WO | WO 0158363 | 8/2001 |
| WO | WO 03001893 | 1/2003 |
| WO | WO 03077772 | 9/2003 |
| WO | WO 2004071307 | 8/2004 |
| WO | WO 2006/044837 A2 | 4/2006 |
| WO | WO 2008/067384 A2 | 6/2008 |
| WO | WO 2008/109087 A1 | 9/2008 |

OTHER PUBLICATIONS

International Preliminary Report on Patentability for PCT/US2010/029798.

International Search Report/Written Opinion for PCT/US2010/029738.

International Preliminary Report on Patentability for PCT/US2010/029738.

International Search Report/Written Opinion for PCT/US2008/064513.

International Preliminary Report on Patentability for PCT/US2008/064513.

Office Action dated Oct. 29, 2010 in related case U.S. Appl. No. 12/125,525.

Office Action dated Mar. 23, 2011 in related case U.S. Appl. No. 12/125,525.

Office Action dated Aug. 23, 2011 in related case U.S. Appl. No. 12/125,525.

Office Action dated Apr. 12, 2012 in related case U.S. Appl. No. 12/753,111.

David J. Desilets et al., Article Entitled "Loop-Anchor Purse-String Versus Endoscopic Clips for Gastric Closure: A Natural Orifice Transluminal Endoscopic Surgery Comparison Study Using Burst Pressures", Journal—Gastrointestinal Endoscopy, vol. 70, No. 6, (2009) pp. 1225-1230.

* cited by examiner

TISSUE ANCHORS AND MEDICAL DEVICES FOR RAPID DEPLOYMENT OF TISSUE ANCHORS

CROSS-REFERENCE TO RELATED APPLICATIONS

This application claims the benefit of U.S. Provisional Application Ser. No. 61/166,364 filed on Apr. 3, 2009, entitled "TISSUE ANCHORS AND MEDICAL DEVICES FOR RAPID DEPLOYMENT OF TISSUE ANCHORS," the entire contents of which are incorporated herein by reference.

FIELD OF THE INVENTION

The present invention relates generally to medical devices, and more particularly relates to tissue anchors for closing perforations in tissue.

BACKGROUND OF THE INVENTION

Perforations in bodily walls may be naturally occurring, or formed intentionally or unintentionally. In order to permanently close these perforations and allow the tissue to properly heal, numerous medical devices and methods have been developed employing sutures, adhesives, clips, staples and the like. Many of these devices typically employ one or more sutures, the strands of which must be brought together and fixed in place in order to close the perforation, and thereafter cut and removed from within the patient's body.

Manually tying suture strands together to close a perforation can be very complex and time consuming. For example, a significant level of skill and coordination is required by the medical professional, especially when the perforation and sutures are difficult to access within the body, such as in endoscopic or laparoscopic procedures. The numerous difficulties with manually tying and cutting sutures are well documented. In order to address these and other issues of manual suture tying and cutting, various automatic suture tying systems have been developed. Unfortunately, such automatic systems are often complex and costly, difficult to use, and limited to use in certain situations.

BRIEF SUMMARY OF THE INVENTION

The present invention provides tissue anchors, as well as related devices and methods, for closing perforations in bodily walls. The tissue anchors are simple and reliable in use, facilitate perforation closure, and are adaptable to a variety of perforation closure situations. One embodiment of a tissue anchor, structured for engagement with a tensioning member, for closing a perforation, constructed in accordance with the teachings of the present invention, generally comprises a crossbar and a strand. The crossbar has first and second opposing ends and defines a longitudinal axis. The strand is connected to the crossbar at a location between the opposing ends. The strand has a length in the range of about 5 mm to about 50 mm extending from a distal end connected to the crossbar to a proximal end having a first connector. The strand and its first connector project away from the longitudinal axis.

Another embodiment of the present invention includes a medical device for closing a perforation. The medical device generally comprises a set of tissue anchors and an elongate tensioning member. Each tissue anchor includes a crossbar and a strand. The crossbar has first and second opposing ends and defines a longitudinal axis. The strand is connected to the crossbar at a location between the opposing ends and projects away from the longitudinal axis. A distal end of the strand is connected to the crossbar and a proximal end of the strand includes a first connector. The elongate tensioning member is structured to selectively engage and disengage the first connector. The strands are capable of being tensioned and fixed together for closing the perforation.

According to more detailed aspects of this embodiment of the medical device, the strand has a length in the range of about 20 mm to about 30 mm.

A method for closing a perforation in a bodily wall of a patient is also provided in accordance with the teachings of the present invention. A medical device, such as the device described above, is provided. Each tissue anchor is passed through the bodily wall adjacent the periphery of the perforation such that the crossbar of each tissue anchor is on a distal side of the bodily wall and the first connector of each tissue anchor is on a proximal side of the bodily wall for selectively engaging and disengaging the elongate tensioning member. The elongate tensioning member engages with the first connector of each strand and the elongate tensioning member is manipulated to position the strands close to one another. The strands are secured together on the proximal side of the bodily wall. The elongate tensioning member disengages from the first connector and is removed from within the patient.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1A:
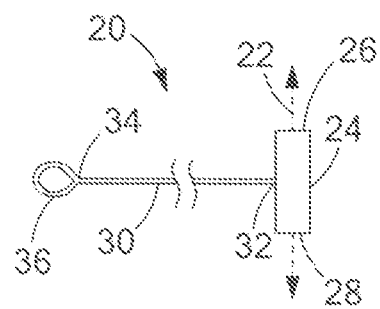
FIG. 1a is a front view of one embodiment of a tissue anchor constructed in accordance with the teachings of the present invention.
Figure 5:
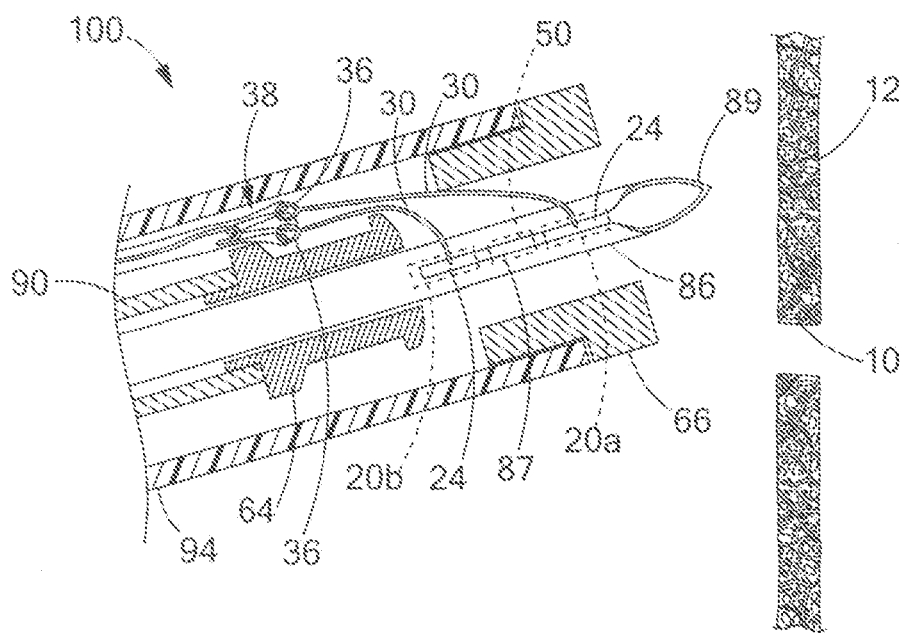
FIGS. 5-9 depict steps in a method for using a medical device in accordance with the teachings of the present invention.
Figure 6:
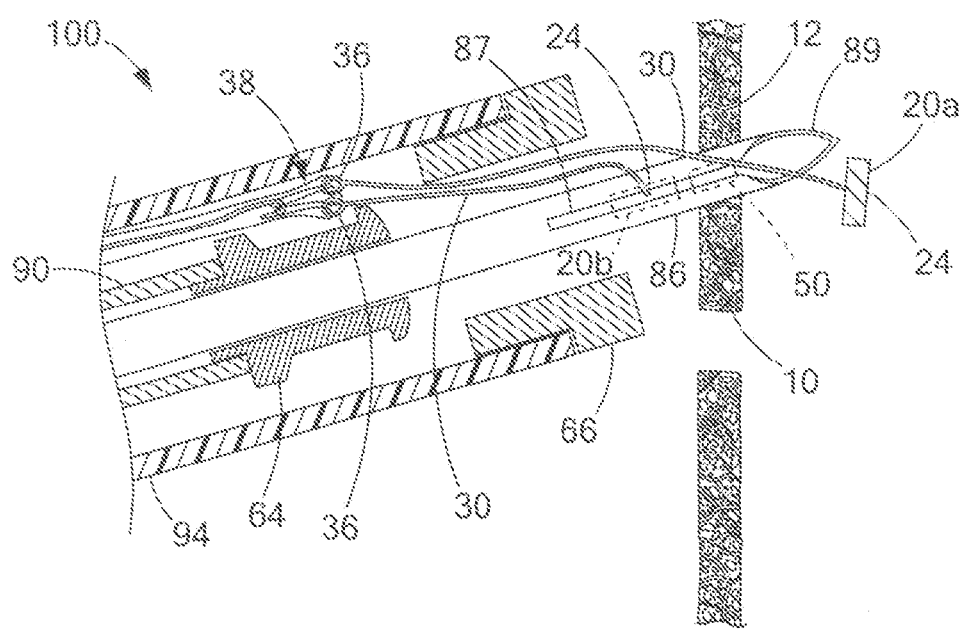
Figure 7:
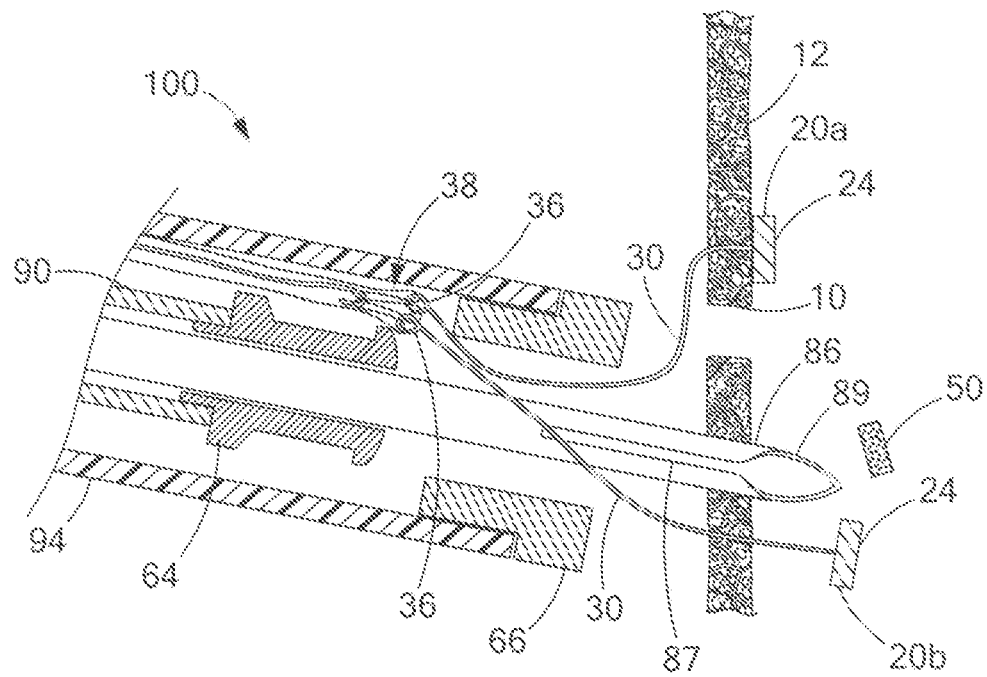

Turning now to the figures, FIG. 1a depicts a tissue anchor 20 constructed in accordance with the teachings of the present invention. The anchor 20 is utilized for closing a perforation 10 in a bodily wall 12 (FIGS. 5-7). The anchor 20 may also be used for apposing tissue, for example, in gastroesophageal reflux disease (GERD) therapy, or bariatric surgery in which an anastomosis is formed, or for use in other procedures. The anchor 20 generally includes a crossbar 24 having opposing ends 26 and 28 and defining a longitudinal axis 22. A flexible strand 30 is connected to the crossbar 24 at a location between the opposing ends 26 and 28 of the crossbar 24. The strand 30 includes a distal end 32 connected to the crossbar 24 and extending away from the longitudinal axis 22 of the crossbar 24 to a proximal end 34 which terminates in a connector 36, discussed in further detail below.

The crossbar 24 is preferably elongated, but may take any form suitable for closing the perforation 10 in the bodily wall 12, including rods, tubes, disc shapes or other elongated or planar shaped members. The crossbar 24 is preferably formed of a tubular cannula, although the crossbar 24 may be a solid cylinder, a metal bar, a plastic molded piece, or any stock materials. The strand 30 is preferably formed from a flexible suture material, although the strand 30 can have other constructions such as a metal wire, including single filament and multi-filament wires, and wound and braided wires, plastic strings, rope and the like.

It will be recognized by those skilled in the art that the strand 30 may be secured to the crossbar 24 using any now known or hereinafter developed attachment means, including mechanical fasteners, adhesives or various welding or soldering techniques. In one preferred construction, the crossbar 24 is formed of a cannula having an opening formed therethrough between opposing ends 26 and 28 and the distal end 32 of the strand 30 is received within the opening in the cannula and crimped in place. Alternatively, the strand 30 may be unitarily and integrally formed with the crossbar 24 as a single piece. Accordingly, the entire tissue anchor 20 may be formed of a single plastic or metal material, and most preferably a resorbable material. For example, the anchor 20, including the crossbar 24 and strand 30, may be injection molded of a permanent material, such as nylon, or a resorbable material. The material of the anchor 20 could also be made radiopaque or echogenic, e.g., by embedding particles within the plastic or selecting a suitable material having inherent or formed radiopaque or echogenic properties.

As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; trimethlyene carbonate; polycaprolactone; poly-beta hydroxy acids such as polyhydroxybutyrate or polyhydroxyvalerate; or other polymers such as polyphosphazines, polyorgano-phosphazines, polyanhydrides, polyesteramides, poly-orthoesters, polyethylene oxide, polyester-ethers (e.g., poly-dioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

The strand 30 preferably has a length in the range of about 5 mm to about 50 mm, and most preferably about 20 mm to about 30 mm. The strand 30 preferably has a diameter less than about 50% of a diameter of the crossbar 24, and most preferably less than about 35%. The strand 30 preferably has a diameter in the range of about 0.20 mm to about 0.35 mm, and most preferably about 0.254 mm. The crossbar 24 preferably has a diameter in the range of about 0.5 mm to about 1.0 mm, and most preferably about 0.8 mm. The crossbar 24 typically has a length in the range of about 3.0 mm to about 10.0 mm. The crossbar 24 and/or the strand 30 may be coated with a low-friction material such as known plastic or hydrophilic coatings.

Figure 1B:
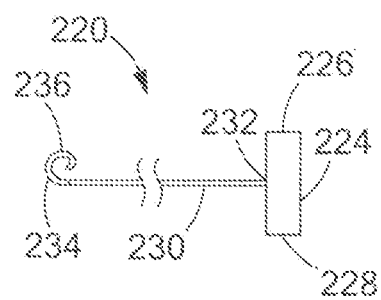
FIG. 1b is a front view of yet another embodiment of a tissue anchor constructed in accordance with the teachings of the present invention.

As illustrated in FIG. 1a, the connector 36 most preferably takes the form of an eyelet or closed loop at the proximal end 34 of the strand 30. The closed loop connector 36 preferably has a diameter in the range of about 0.5 mm to about 1.5 mm. The connector 36 can have an alternative shape, such as that depicted in FIG. 1b. FIG. 1b depicts an embodiment of a tissue anchor 220 in accordance with the teachings of the present invention and having a description similar to that of FIG. 1a, and in which similar components are denoted by similar reference numerals increased by 200. In this embodiment, the connector 236 takes the form of a J-shaped hook.

The connector 36 is structured to receive a tensioning member 38 (FIGS. 2a-c) for aiding in deployment of the anchor 20. The connector 36 may be formed from a flexible suture material, metal wire, plastic, rope or any suitable resorbable material. As shown in FIG. 1a, the closed loop connector 36 is preferably formed integrally with the strand 30. The closed loop connector 36 is flexible and is capable of stretching or adjusting its shape and orientation when tensioned by the tensioning member 38. Alternatively, the connector 36 may be formed from a different material than the strand 30, may have a greater thickness than the strand 30, and may be secured to the strand 30 using any suitable means, including mechanical fasteners, tying, bonding, welding, or adhesives. For example, in order for the J-shaped hook connector 236 of FIG. 1b to maintain its shape when tensioned by a tensioning member, the connector 236 is preferably made of a stronger, more rigid material than the strand 230 such as a rigid plastic or metal material. In addition, the connector 36 preferably has a smooth, rounded shape so that the anchor 20 is atraumatic to other surrounding tissues.

Figure 2A:
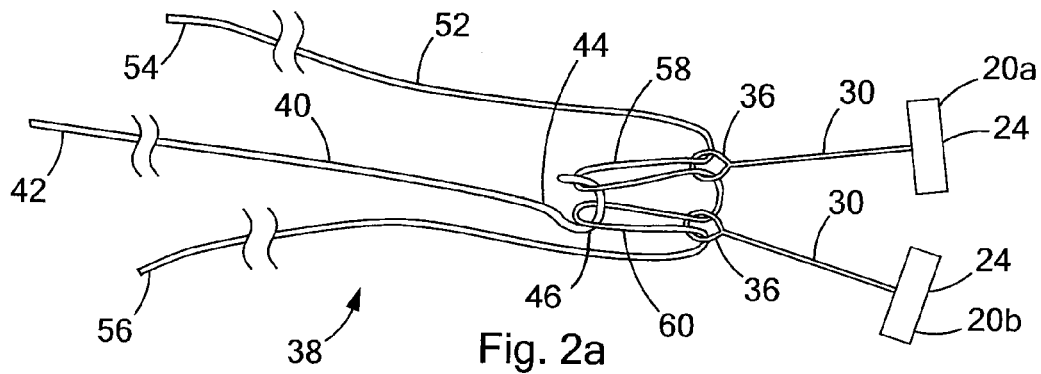
FIG. 2a is front view of one embodiment of a medical device constructed in accordance with the teachings of the present invention.
Figure 2B:
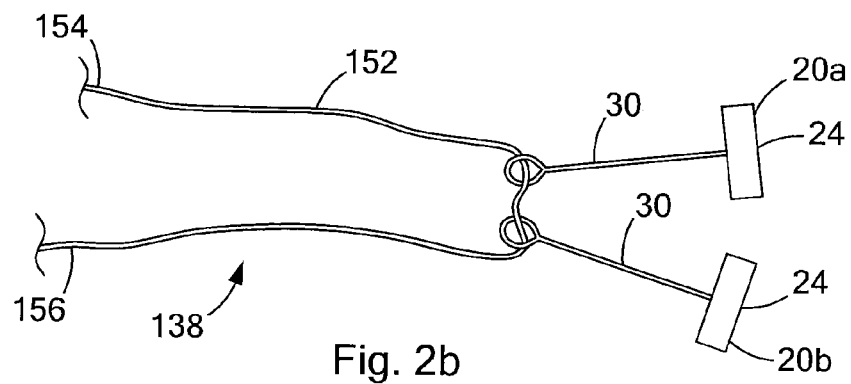
FIG. 2b is a front view of another embodiment of a medical device constructed in accordance with the teachings of the present invention.
Figure 2C:
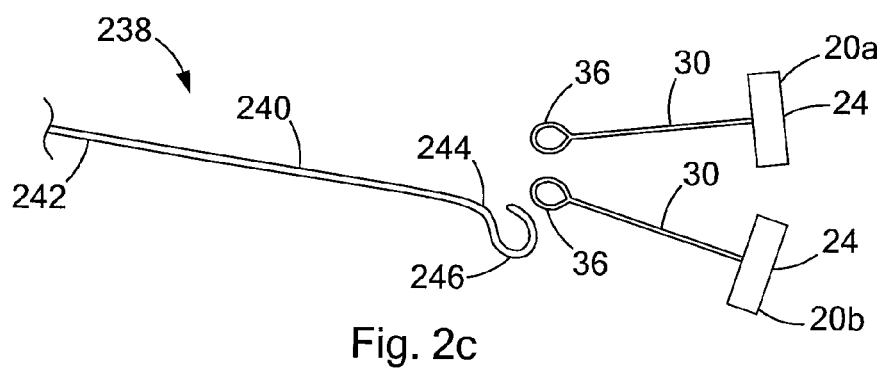
FIG. 2c is a front view of yet another embodiment of a medical device constructed in accordance with the teachings of the present invention.

Turning now to FIGS. 2a-c, a pair of tissue anchors 20a and 20b is depicted with various embodiments of tensioning members 38, 138, and 238 configured to selectively engage and disengage the connectors 36. As depicted in FIG. 2a, the tensioning member 38 includes a suture 52 in combination with an elongate holding member 40. The suture 52 and elongate holding member 40 of FIG. 2a are shown in use with anchors 20a and 20b having connectors 36 in the form of a closed loop, as depicted in the embodiment of FIG. 1a.

The suture 52 includes first and second ends 54 and 56 which are preferably located and maintained outside of the body. The first and second ends 54 and 56 can be fixed within a handle (not shown) at a proximal end of the tissue anchor delivery device (FIG. 4), for example, by a tuohy borst connector or clamp. The suture 52 is preferably pre-loaded through the closed loop connectors 36 such that a section of the suture 52 is pulled through each of the closed loops connectors 36 and maintained by the elongate holding member 40. Thus, the suture 52 preferably passes through each closed loop connectors 36 twice to form folded over looped sections 58 and 60. These folded over looped sections 58 and 60 are of a sufficient length to provide adequate slack in the suture 52 during distal advancement and separate positioning of the tissue anchors 20a and 20b.

As depicted in FIG. 2a, the suture 52 extends from the first end 54 and is folded over to form the first looped section 58; the suture 52 extends from the first looped section 58 and is folded over to form the second looped section 60; and the suture 52 extends from the second looped section 60 to the second end 56. The first looped section 58 is slidably received within the closed loop connector 36 of the first anchor 20a of the pair of anchors and the second looped section 60 is slidably received within the closed loop connector 36 of the second anchor 20*b* of the pair of anchors. The elongate holding member 40 includes a proximal end 42 and a distal end 44 terminating with a connector 46 structured to selectively engage and disengage the first and second looped sections 58 and 60 of the suture 52. The suture 52 may be of a single filament or multi-filament constructions and preferably has a diameter in the range of about 0.20 mm to about 0.35 mm.

It will be recognized by those skilled in the art that the connector 46 may take on any suitable shape or form suitable for selective engagement and disengagement with the looped sections 58 and 60. Preferably, the connector 46 at the distal end 44 of the elongate member 40 is hook shaped, e.g., a J-shaped hook as shown.

As depicted in the alternate embodiment of FIG. 2*b*, the tensioning member 138 includes a suture 152 having first and second ends 154 and 156 which extend through the tissue anchor delivery device and are located and maintained outside of the body proximate a proximal end of the delivery device for manipulation by the physician. In this embodiment, the suture 152 extends from the first end 154 through the first and second closed loop connectors 36 of the pair of anchors 20*a* and 20*b*, respectively. The tensioning member 138 including the suture 152 may be used in conjunction with anchors having connectors other than the closed loop connectors 36 illustrated FIG. 2*b*. For example, the suture 152 may selectively engage hooked connectors, such as the J-shaped hook connector 236 illustrated in FIG. 1*b*, in which the suture 152 would be threaded through the hooked connector 236. The suture 152 may be of a single filament or multi-filament constructions.

As depicted in the alternate embodiment of FIG. 2*c*, the tensioning member 238 includes an elongate holding member 240 having a proximal end 242 and a distal end 244 terminating with a connector 246 structured to selectively engage and directly disengage the first and second closed loop connectors 36 of the pair of anchors 20*a* and 20*b*, respectively. Preferably, the connector 246 at the distal end 244 of the elongate member 240 is a J-shaped hook. The elongate holding member 240 having the connector 246 may be used in conjunction with anchors having connectors other than the closed loop connectors 36 illustrated in FIG. 2*c*. For example, the connector 246 of the holding member 240 may selectively engage a hook shaped connector, such as the J-shaped hooked connector 236 of FIG. 1*b*. It will be recognized by those skilled in the art that the connector 246 may take on any suitable shape or form suitable for selective engagement and disengagement with the various connectors 36. For example, the connector 246 could be a ringlet or closed loop, while the connectors 36 could be hook shaped (see FIG. 1*b*). These and other variations will be readily apparent to the skilled artisan.

Figure 3:
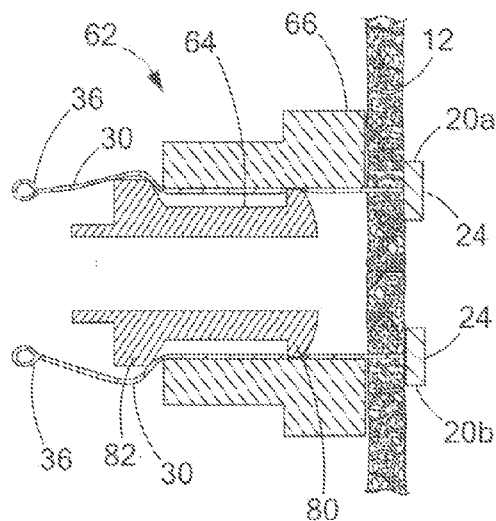
FIG. 3 is a cross-sectional view of tissue anchors, in accordance with the teachings of the present invention, shown closing a perforation.
Figure 4:
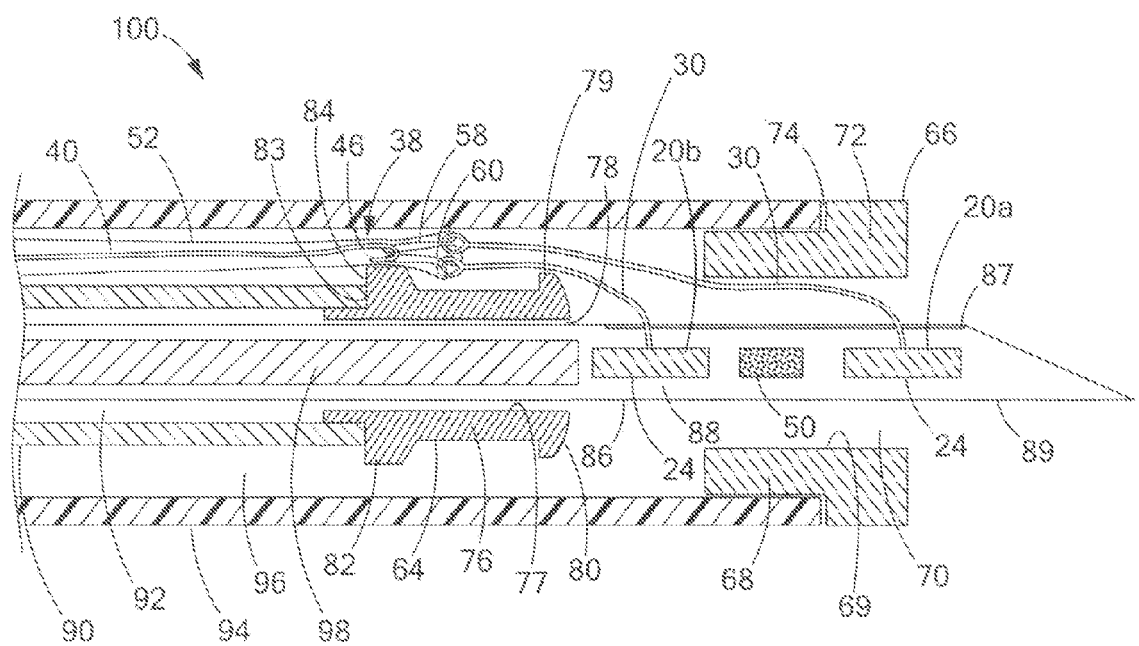
FIG. 4 is a plan view, partially in cross-section, of a medical delivery device constructed in accordance with the teachings of the present invention.

Turning now to FIGS. 3 and 4, the tissue anchors 20 are preferably deployed as a set of anchors including at least two anchors 20*a* and 20*b*. The tensioning member 38 aids in positioning the anchors 20*a* and 20*b* during delivery of the anchors 20*a* and 20*b* through tissue of the bodily wall 12 and is removed thereafter, as will be described in more detail below. As best seen in FIG. 3, the crossbars 24 of the anchors 20*a* and 20*b* are positioned on a distal side of the bodily wall 12, while the majority of the strands 30 connected to the crossbars 24, including the connectors 36, are positioned on a proximal side of the bodily wall. After the anchors 20*a* and 20*b* are positioned through the tissue of the bodily wall 12, the strands 30 of the anchors 20*a* and 20*b* are brought together, via the tensioning member 38, and fixed in place, via a suture lock 62, in order to close the perforation 10. Thereafter, the tensioning member 38 is removed. Thus, rather than employing a separate suture or a plurality of individual sutures to fix the anchors to the bodily wall (which must be fixed in place in order to close the perforation, and thereafter manually cut and removed) the anchors 20*a* and 20*b* are fixed together directly, via the strands 30 and the suture lock 62. Thus, the construction of the anchors 20*a* and 20*b*, including strands 30 with connectors 36, alleviates the many difficulties associated with manually cutting sutures used to fix the anchors together.

Referring to FIG. 4, a medical delivery device 100 for employing the anchors 20*a* and 20*b* and the lock 62, in accordance with the teachings of the present invention, includes a needle 86 having a needle lumen 88 sized to slidably receive the tissue anchors 20*a* and 20*b*. Preferably, a resorbable spacer member 50 is positioned between the anchors 20*a* and 20*b* within the needle lumen 88 near the distal end 89 of the needle 86. The needle 86 includes a needle slot 87 sized to receive the strands 30 of the anchors 20*a* and 20*b*. The medical delivery device 100 may include a set of more than two anchors and more than one spacer members. The longitudinal length of the needle slot 87 is dependent upon the number of anchors and the length of the crossbars and the number of spacer members positioned between the anchors and the length of the spacer members such that the needle slot 87 is capable of receiving the strands 30 connected to each of the crossbars 24 positioned within the needle lumen 88. A pusher 98 is slidably received within the needle lumen 88 to engage the proximal-most anchor, the anchor 20*b* in FIG. 4, and deploy the anchors 20*a* and 20*b*, and the spacer member 50 positioned therebetween, from the delivery device 100.

The medical device 100 further includes an inner sheath 90 having a lumen 92 sized to slidably receive the needle 86 and an outer sheath 94 having a lumen 96 sized to slidably receive the inner sheath 90. The strands 30 of the anchors 20*a* and 20*b* extend away from the longitudinal axis 22 of the crossbars 24 of the anchors 20*a* and 20*b*, through the needle slot 87 and proximally within the outer sheath lumen 96. A tensioning member 38, in accordance with the teachings of the present invention, is slidably received within the outer sheath lumen 96 to selectively engage and disengage the connectors 36 of the strands 30 of the anchors 20*a* and 20*b*. While the tensioning member 38 of FIG. 2*a*, including the suture 52 and the elongate holding member 40, is illustrated as part of the medical delivery device 100 in FIGS. 4-9, the tensioning members 138 or 238 of FIGS. 2*b* and 2*c*, respectively, may be employed as part of the medical delivery device 100. Similarly, the anchor 220 of FIG. 1*b* having a J-shaped connector 236 may be delivered using the medical delivery device 100 in accordance with the teachings of the present invention.

The inner and outer sheaths 90 and 94 are preferably formed of a plastic such as polytetrafluorethylene (PTFE), expanded polytetrafluorethylene (EPTFE), polyethylene ether ketone (PEEK), polyvinylchloride (PVC), polycarbonate (PC), polyamide including nylon, polyimide, polyurethane, polyethylene (high, medium or low density), or elastomers such as Santoprene®, including multi-layer or single layer constructions with or without reinforcement wires, coils or filaments. The needle 86, inner and outer sheaths 94 and 90, the pusher 98, and the tensioning member 38, including the suture 52 and the holding member 40, are preferably elongated structures that are flexible, allowing navigation within a patient's body such as during endoscopic or laparoscopic procedures. As such, a suitable handle or control mechanism will be connected to the proximal ends of the needle 86, sheaths 90 and 94, and pusher 98 for relative translation of these components by the medical professional, as is known in the art.

Preferably, the medical device 100 further includes an over-the-needle suture lock 62 for fixing the strands 30 of the anchors 20*a* and 20*b* after delivery of the anchors 20*a* and 20*b* through the bodily wall 12. An over-the-needle suture lock 62, in accordance with the teachings of the present invention, allows the strands 30 of the set of anchors 20*a* and 20*b* to be preloaded within the suture lock 62 during delivery of the anchors 20*a* and 20*b* through the bodily wall 12. The suture lock 62 generally includes a locking pin or plug 64 and a retaining sleeve 66 which cooperate to fix the strands 30 of the anchors 20*a* and 20*b* relative to tissue of the bodily wall 12 for closing the perforation 10 in the bodily wall 12. The retaining sleeve 66 and plug 64 may have a circular cross-section, or any other cross-sectional shapes including triangular, square, etc.

As best seen in FIGS. 4-9, the retaining sleeve 66 generally includes a tubular body 68 having an interior surface 69 defining an interior passageway 70. A peripheral rim 72 is formed at a distal end of the tubular body 68, and defines a shoulder 74 which is used for placement of the retaining sleeve 68, as will be discussed in further detail herein. Generally, the retaining sleeve 68 receives the strands 30 of the anchors 20*a* and 20*b* within the interior passageway 70. The strands 30 are then fixed in place using the plug 64, which is designed to fit within the passageway 70 and pinch or compress the strands 30 of the anchors 20*a* and 20*b*. It will also be recognized that the plug 64 may have many configurations (e.g. regular or irregular shapes), and constructions (e.g. cast, molded, machined, wound (such as with wire), etc.) so long as a portion of the plug 64 cooperates with the retaining sleeve 66 to fix the strands 30. Preferably, the plug 64 and the retaining sleeve 66 are formed from stainless steel or any other suitable metal or plastic material known in the art.

As best seen in FIGS. 4-9, the plug 64 generally includes a main body 76 having an interior surface 77 defining an interior passageway 78 sized to slidably receive the needle 86. The main body 76 includes a grip 80 and a stop 82, each extending radially from the main body 76. In the illustrated embodiment, the grip 80 is formed at a distal end of the plug 64, although it could be moved proximally along the length of the main body 76. The grip 80 defines an annular edge 79 that is used to engage the strands 30 of the anchors 20*a* and 20*b*. The stop 82 is longitudinally spaced from the grip 80 and is used to control the position of the plug 64 within the retaining sleeve 66. The stop 82 generally includes a proximally facing surface 83 defining a shoulder 84 which is used to position the plug 64. The stop 82 is positioned relative to the grip 80 to prevent the grip 80 from passing completely through the internal passageway 70 of the retaining sleeve 66. While the length of the strands 30 of the tissue anchors 20 is preferably between about 5 mm and 50 mm, the length of the strands 30 should be such that the connectors 36 of the strands 30 exit the suture lock 62 to provide sufficient engagement of the strands 30 between the plug 64 and retaining sleeve 66.

As depicted in FIGS. 4-7 the inner sheath 90 is sized and positioned to abut the shoulder 84 of the plug 64 and the outer sheath 94 is sized and positioned to abut the shoulder 74 of the retaining sleeve 66. Translation of the inner sheath 90 relative to the outer sheath 94 causes the plug 64 to slide over-the-needle 86 and to be received within the passageway 78 of the retaining sleeve 66 to engage the strands 30 of the anchors 20*a* and 20*b* between the main body 76 of the plug 64 and the interior surface 77 of the retaining sleeve 66 to fix the strands 30.

Further details of the needle assembly and the over-the-needle suture lock 62 may be found in U.S. Provisional Application No. 61/166,361 entitled "Medical Devices, Systems, and Methods for Rapid Deployment and Fixation of Tissue Anchors" to Ducharme, the entire contents of which are incorporated by reference herein.

The medical device 100 may be sized to be used through an accessory channel of an endoscope or alongside an endoscope, or in combination with other devices used in conjunction with endoscopes, for example, endoscopic suction devices or fluid injection devices.

A method of closing the perforation 10, in accordance with the teachings present invention, includes passing each tissue anchor 20*a* and 20*b* through the tissue of the bodily wall 12 adjacent the periphery of the perforation 10, as shown in FIGS. 5-7. Preferably, the anchors are sequentially positioned around the perforation 10. As shown, the anchors 20*a* and 20*b* are positioned on opposing sides of the perforation 10. As previously noted, a plurality of anchors including more than the two anchors 20*a* and 20*b* may be sequentially positioned around the perforation 10.

As illustrated in FIG. 5, the medical delivery device 100, in accordance with the teachings of the present invention, is delivered to a position proximate the tissue of the bodily wall 12. The anchors 20*a* and 20*b* are disposed within the needle lumen 88 at the distal end 89 of the needle 86 and a resorbable spacer member 50 is disposed between the anchors 20*a* and 20*b*. Spaces between the spacer member 50 and the anchors 20*a* and 20*b* have been shown for clarity, but the spacer member 50 and the anchors 20*a* and 20*b* would generally be abutting end-to-end within the needle lumen 88. The strands 30 of the anchors 20*a* and 20*b* are received within the needle slot 87 and project away from the longitudinal axis 22 of the anchor crossbars 24. Preferably, the needle 86 is slidably received within the inner sheath lumen 92, and the tensioning member 38 is pre-engaged with the connectors 36 of the anchor strands 30 extending from the needle lumen 88, prior to being slidably received within the outer sheath lumen 96. Thus, the needle 86 within the inner sheath 90 and the tensioning member 38 are preferably pre-engaged and loaded into the outer sheath 94 together and advanced toward a distal end 95 of the outer sheath 96 prior to positioning of the medical delivery device 100. Thus, as depicted in FIGS. 4-7, the tensioning member 38 is disposed within the outer sheath lumen 96 and is in selective engagement with the connectors 36 of the strands 30 of the anchors 20*a* and 20*b*.

The method illustrated in FIGS. 5-7 depicts a medical delivery device 100 including, as an example, the tensioning member 38 of FIG. 2*a*. In this example, once positioned near the distal end 95 of the outer sheath 96, the elongate holding member 40 maintains its hold on the connectors 36 of the anchor strands 30 via the first and second looped sections 58 and 60 of the suture 52. The first and second ends 54 and 56 of the suture 52 are preferably maintained within a proximal handle (not shown) of the device 100 while the physician maintains a hold of and manipulates the elongate holding member 40. The folded over looped sections 58 and 60 are preferably of a sufficient length to provide adequate slack in the suture 52 during separate positioning of the tissue anchors 20*a* and 20*b*.

As illustrated in FIG. 5-6, the needle 86 is deployed through the tissue of the bodily wall 12 by translating the needle 86 relative to the inner and outer sheaths 90 and 94. The distal-most tissue anchor, the anchor 20*a* in FIGS. 4-5, is then deployed from the needle 86 by translating the anchor 20*a* relative to the needle 86 so that the anchor 20*a* exits the needle lumen 88. As shown in FIGS. 4-5, the anchors 20*a* and 20*b*, and the spacer member 50 positioned therebetween, are shown aligned within the needle lumen 88 along a longitudinal axis of the needle lumen 88 such that the pusher 98 may be slidably received within the inner sheath lumen 92 and used to engage and press on the proximal-most anchor, anchor 20b in FIGS. 4-7, which will in turn transmit force through the spacer member 50 and the distal-most anchor 20a, thus advancing the distal-most anchor 20a out of the needle lumen 88. As the anchor 20a exits the needle lumen 88, the strand 30 of the anchor 20a is released from the needle slot 87.

Accordingly, it will be recognized that a large number of tissue anchors and spacer members may be employed within the medical device 100, and the longitudinal length of needle slot 87 can be sized to accommodate any number of anchor strands 30. In this manner, the medical device 100 need not be withdrawn to be reloaded. The method may therefore include withdrawing the needle 86 from the bodily wall by translating the needle 86 proximally, and then repeating the steps of translating the needle 86 through the tissue 12 and deploying a tissue anchor therethrough.

Turning to FIG. 7, the needle 86 is retracted back through the bodily wall 12 by translating the needle 86 proximally, repositioned at a different position about the perforation 10, and redeployed back through the tissue of the bodily wall 12 by translating the needle 86 relative to the inner and outer sheaths 90 and 94. The pusher 98 is then further advanced distally to deploy the spacer member 50 and the proximal anchor 20b, wherein the strand 30 of the anchor 20b is released from within the needle slot 87. The spacer member 50 is then resorbed within the patient's body.

Figure 8:
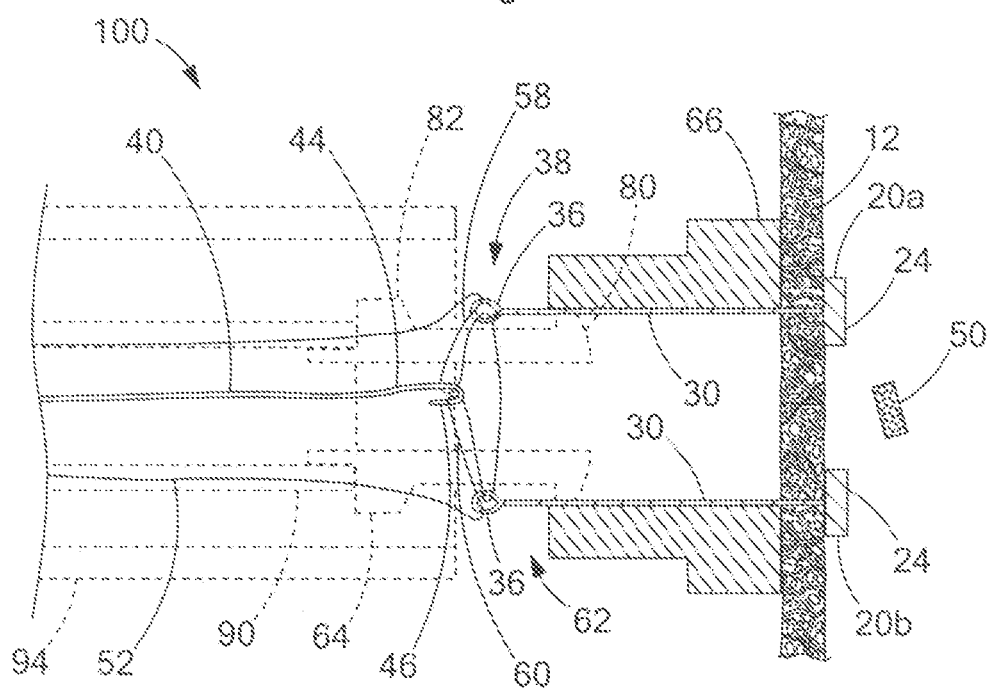

After the anchors 20a and 20b are deployed on the distal side of the bodily wall 12, the needle 86 is retracted back through to the proximal side of the bodily wall 12 and removed from within the inner sheath lumen 92. The elongate holding member 40 is used to tension the strands 30 of the anchors 20a and 20b to bring the strands 30 together to close the perforation 10. Preferably, the elongate holding member 40 is retracted, applying a pulling force on the first and second looped sections 58 and 60 of the suture 52, which in turn applies a pulling force on the connectors 36, thus tensioning the strands 30 of the anchors 20a and 20b to reduce the distance between the anchors 20a and 20b and compress the bodily wall 12 around the perforation 10, as depicted in FIGS. 8 and 9.

Figure 9:
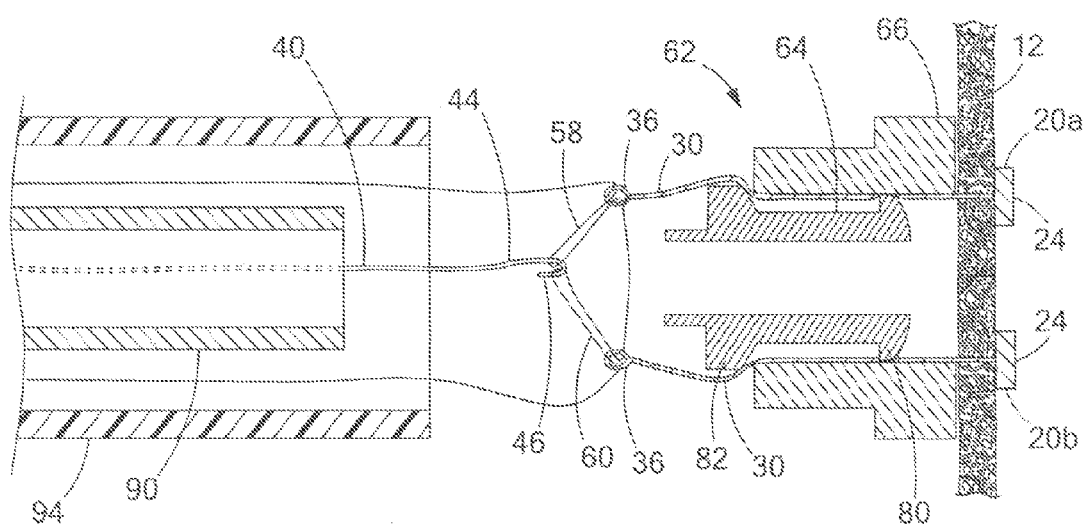

As best seen in FIG. 9, the strands 30 of the anchors 20a and 20b are secured to maintain the compression of the bodily wall 10, such as through the use of a suture lock. Preferably, the stands 30 are fixed through the use of an over-the-needle suture lock 62, in accordance with the teachings of the present invention, described in detail above and illustrated in FIGS. 4-9. Alternatively, other suture locks may be employed to fix the strands 30, such as the suture locks disclosed in copending U.S. patent application Ser. Nos. 12/125,525 and 12/191,001, the disclosures of which are incorporated herein by reference in their entirety. It will be recognized that any now known or future developed method for securing the strands 30 of the anchors 20a and 20b may be employed, such as knotting, tying, clamps, rivets and the like. After the anchors 20a and 20b have effectively closed the perforation 10 in the bodily wall 12 and the stands 30 are secured, the delivery device 100, including the tensioning member 38, is removed from within the patient. In the example in FIGS. 8-9, the holding member 40 is unhooked from the first and second looped sections 58 and 60 and the suture 52 is removed by opening or releasing the tuohy borst connector or clamp of the proximal handle of the delivery device and pulling one end of the suture 52 while releasing the opposing end of the suture. In this manner, the suture 52 slides through the closed loop connectors 36 as it is removed from the patient.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for closing a perforation in a bodily wall of a body, the medical device comprising:
   a set of tissue anchors, the set of tissue anchors including a first tissue anchor and a second tissue anchor, each tissue anchor including a crossbar and a strand, the crossbar having opposing ends and defining a longitudinal axis, the strand connected to the crossbar at a location between the opposing ends and projecting away from the longitudinal axis, the strand having a distal end connected to the crossbar and a proximal end having a first connector; and
   an elongate tensioning member structured to selectively engage and disengage the first connector, the strands capable of being tensioned and fixed together for closing the perforation, the elongate tensioning member including an elongate suture having opposed first and second ends, wherein the suture selectively engages and disengages the first connectors of the tissue anchors;
   wherein the elongate suture extends from the first end to a first portion folded over to form a first looped section, from the first looped section to a second portion folded over to form a second looped section, and from the second looped section to the second end, and wherein the first connectors of the first and second tissue anchors selectively receive the first and second looped sections, and wherein the device further includes an elongate holding member selectively engaging the first and second looped sections while the first and second looped sections are received by the first connectors.

2. The medical device of claim 1, wherein the strand is fixedly attached to the crossbar.

3. The medical device of claim 1, wherein the strand and the crossbar are integrally and unitarily formed as a single piece.

4. The medical device of claim 1, wherein the strand has a length in the range of about 20 mm to about 30 mm.

5. The medical device of claim 1, further comprising a suture lock for fixing the strands together.

6. The medical device of claim 1, wherein the first connector is a closed loop.

7. The medical device of claim 1, wherein the elongate tensioning member includes a distal end having a second connector, the first and second connectors structured to selectively engage and disengage each other.

8. The medical device of claim 7, wherein the second connector is a J-shaped hook.

9. The medical device of claim 1, wherein the elongate suture includes an intermediate portion located between the first and second ends, wherein the intermediate portion of the suture is configured to selectively engage and disengage the first connector by the medical professional releasing at least one of the first and second ends.

10. The medical device of claim 1, wherein the first connectors of the first and second tissue anchors have first and second closed loops, respectively, wherein the first and second closed loops selectively receive the first and second looped sections, respectively.

11. The medical device of claim 1, wherein the first connector is in the shape of one of a J-shaped hook and a closed loop.

12. The medical device of claim 1, wherein each of the first connectors receive two portions of the elongate suture to form the looped sections.

13. The medical device of claim 1, wherein the first connectors receiving the first and second looped sections each includes the elongate suture passing through the first connector, folding over, and again passing through the first connector.

14. The medical device of claim 12, wherein each first connector includes a single aperture.

15. The medical device of claim 13, wherein each first connector includes a single aperture.

* * * * *